United States Patent

Scholler et al.

(10) Patent No.: US 6,899,707 B2
(45) Date of Patent: May 31, 2005

(54) APPLANATION LENS AND METHOD FOR OPHTHALMIC SURGICAL APPLICATIONS

(75) Inventors: Gordon Scott Scholler, Poway, CA (US); R. Kyle Webb, Escondido, CA (US)

(73) Assignee: Intralase Corp., Irvine, CA (US)

(*) Notice: Subject to any disclaimer, the term of this patent is extended or adjusted under 35 U.S.C. 154(b) by 0 days.

(21) Appl. No.: 09/896,429

(22) Filed: Jun. 29, 2001

(65) Prior Publication Data

US 2002/0103482 A1 Aug. 1, 2002

Related U.S. Application Data

(63) Continuation-in-part of application No. 09/772,539, filed on Jan. 29, 2001.

(51) Int. Cl.[7] .............................................. A61B 18/18
(52) U.S. Cl. ............................... 606/5; 606/4; 606/166
(58) Field of Search ................................. 606/4–6, 166

(56) References Cited

U.S. PATENT DOCUMENTS

| | | | |
|---|---|---|---|
| 5,171,254 A | | 12/1992 | Sher |
| 5,282,088 A | * | 1/1994 | Davidson ..................... 359/664 |
| 5,336,215 A | | 8/1994 | Hsueh et al. |
| 5,359,373 A | | 10/1994 | Koester et al. |
| 5,549,632 A | * | 8/1996 | Lai ............................... 606/5 |
| 5,556,417 A | | 9/1996 | Sher |
| 5,984,915 A | | 11/1999 | Loeb et al. |
| 6,140,630 A | | 10/2000 | Rhodes |
| 6,254,595 B1 | * | 7/2001 | Juhasz et al. .................. 606/5 |
| 6,325,792 B1 | * | 12/2001 | Swinger et al. ................ 606/4 |
| 2002/0103481 A1 | * | 8/2002 | Webb et al. .................... 606/5 |

FOREIGN PATENT DOCUMENTS

WO    WO 01/44871 A1    6/2001

OTHER PUBLICATIONS

Edmund Optics 'Tech Spec for Fused Silica windows, High Performance UV Optics–PCV; High Performance UV Optics–DCV; High Performance UV Optics–DCX; and High Performance UV Optics–PCX.' . http://www.edmundoptics.com/onlinecatalog/search/index.cfm.*
Dynasil "Precision Optics Materials Fabrication." http://www.dynasil.com/.*
PCT Search Report dated Sep. 12, 2002.
Mitsutoshi Ito, et al.; *"Picosecond Laser In Situ Keratomileusis With a 1053–nm Nd: YLF Laser"*, Journal of Refractive Surgery vol. 12 Sep./Oct. 1996.
Specifications on Lens Material from Dynasil Website, available at least as early as May 19, 2001.
Marketing Materials for Fused Silica.
Information on the Optical Properties of Dynasil Synthetic Fused Silica, available at least as early as May 30, 2001.

* cited by examiner

*Primary Examiner*—A. Farah
(74) *Attorney, Agent, or Firm*—Fulbright & Jaworski L.L.P.

(57) ABSTRACT

An improved applanation lens and method for use in an interface between a patient's eye and a surgical laser system does not discolor or lose light transmittance when subjected to gamma radiation. The improved applanation lens has an applanation surface configured to contact the eye upon application of a pressure. The lens is formed of high purity silicon dioxide ($SiO_2$) with purity great enough to resist discoloration upon prolonged irradiation by high-energy radiation such as UV, x-rays, gamma rays or neutrons, and is preferably a fused silica.

12 Claims, 7 Drawing Sheets

APPLANATION LENS AND METHOD FOR OPHTHALMIC SURGICAL APPLICATIONS

CROSS REFERENCE TO RELATED APPLICATIONS

The present application is a continuation-in-part of co-pending U.S. patent application Ser. No. 09/772,539 filed Jan. 29, 2001, which is commonly owned by the assignee of the present application, the entire contents of which are expressly incorporated by reference.

FIELD OF THE INVENTION

The present invention relates to an improved applanation lens for an interface device for ophthalmic laser surgery and, more particularly, an applanation lens formed of a material that is biocompatible with the cornea and does not discolor and/or have reduced transmittance with respect to its ability to transmit light energy generated by a laser beam during ophthalmic surgery. An applanation lens is a lens with an applanation surface configured to contact the eye and applanate or flatten the anterior surface of the eye upon application of a pressure. An applanation lens for use with laser surgery must be relatively free from aberrations, both spherical aberrations (which relates to points on the optical axis of the laser beam) and coma (which relates to points that are off-axis).

BACKGROUND OF THE INVENTION

In recent years, significant developments in laser technology have led to its application in the field of ophthalmic surgery. In particular, laser surgery has become the technique of choice for ophthalmic surgical applications. In certain ophthalmic laser procedures, surgeons use a mechanical device termed a microkeratome to cut a layer of the anterior surface of the cornea in order to expose the underlying corneal stroma to which the laser is applied. However, complications surrounding the use of the microkeratome and its metal blade have resulted in research into improved techniques that are performed exclusively by a laser system. Such all-laser techniques obviate the need for mechanical devices pre- or post-operatively, and provide significantly improved precision.

Despite these advances in laser technology, the use of such systems for ophthalmic surgical procedures remains fraught with substantial mechanical limitations, particularly in the area of developing a stable interface between an incident laser beam and the eye of a patient. Ophthalmic surgery is a precision operation and requires a very precise coupling between the surgical tool (i.e., the laser beam) and the region to be disturbed (i.e., a portion of the patient's eye). Even a very small movement of the eye with respect to the intended focal point of the laser beam can not only lead to non-optimal results, but might even result in permanent damage to non-renewable tissue within the eye, leading to precisely the opposite result than that desired. Given that eye movement is often the result of autonomic reflex, it should be understood that there must be some means of stabilizing the position of a patient's eye with respect to an incident laser beam in order to avoid the intolerable consequence of relative movement.

Heretofore, the major technique used to compensate for relative eye motion with respect to an incident laser beam has been to have the patient focus on a stationary target. This involves providing a visual target to the eye undergoing surgery, and requiring that the patient retain focused on the perceived target feature. While this technique has provided some small benefit, it places all of the burden of minimizing relative motion upon the patient, and does not allow for any gross autonomic reflex motions, e.g., as when the patient might be startled. In this technique, the target provides optical interface, while the patient's conscious responses provide the feedback mechanism.

An additional technique involves the use of an optical eye tracking apparatus, whereby a selected eye feature is targeted for monitoring by an optical device, and as the targeted feature displaces as the result of eye movement, its displacement is characterized and fed into the incident laser beam control apparatus as a compensation signal. This second technique offers a substantial improvement over the first, particularly when it is implemented in addition to a patient-driven target focusing mechanism. However, such systems are inordinately expensive since a second, completely independent optical path must be provided between a patient's eye and a surgical apparatus in order to accommodate the eye tracking apparatus. Further expense and complexity are incurred when it is considered that an eye tracking apparatus requires an additional software component in order to be operative, which software component must be integrated into a laser delivery system. Considerations of interoperability must be met as well as the provision for an automatic shutdown of the laser system in the event of the loss of target feature lock.

Accordingly, a simple mechanical system, if properly designed, is able to best meet the imperatives of interfacing a laser delivery system with a target object. If the goal is to minimize relative analog motion, an analog stabilization device would necessarily offer the most advantageous solution.

In this regard, certain mechanical stabilization devices have been proposed, particularly, a corneal applanation device which is the subject of U.S. patent application Ser. No. 09/172,819, filed Oct. 15, 1998 and commonly owned by the assignee of the present invention, the entire contents of which are expressly incorporated herein by reference. Such a mechanical device directly couples a patient's eye to the laser's delivery system being affixed to both the laser and the anterior surface of a patient's cornea. The corneal coupling, in these devices, is typically implemented by lowering an applanation fixture over the anterior surface of the cornea under pressure. It is assumed in these forms of devices that pressure applied normal to the corneal surface will restrict conventional motion of the cornea thereby stabilizing the eye along a major access normal to the device.

However, although this assumption may hold true in a large number of cases, it certainly does not have universal application. Moreover, in the cases where it does hold, the device/cornea interface should be established with the iris centered, for best results. The actual establishment of an effective device/corneal interface is an exercise in trial-and-error, resulting in a great deal of frustration to doctor and patient, as well as considerable eye fatigue. For ophthalmic laser procedures where eye tissue is to be photodisrupted, it is extremely important for the laser beam to be properly focused to a specific focal spot in the tissue that is to be effected. Not only is it extremely important to have good focal definition, but also for the focal point to have the proper dimensionality (i.e., the correct spot diameter and shape). In order to accommodate this, it is necessary for the laser beam to be as free from aberrations as possible. In particular, for ophthalmic laser procedures involving the cornea, it happens that the spherical geometry of the cornea introduces optical aberrations as a result of its shape, which are separate and distinct from aberrations introduced by the laser's own optical system. Significantly, these corneal induced aberrations distort the definition of the focal spot of a laser beam as the beam is focused to a position within corneal tissue.

Due to the spherical geometry of the anterior surface of the cornea, two specific types of aberrations are of particular importance with regard to beam distortion; spherical aberration (which relates to points on the optical axis of the laser beam) and coma (which relates to points that are off-axis). Spherical aberration and coma are similar to one another in that they both arise from a failure to image or focus optical ray traces onto the same point. Spherical aberration relates to a distortion that can be characterized as radial in nature, with some radial directions being stretched while other radial directions are shrunk, converting thereby, an ideally circular spot into an elliptical spot. Coma distortion, on the other hand, implies an elongation along one radius in the shape of a circle, resulting in a "cometlike" shape. Accordingly, any structure which interfaces between a curved, anterior surface of the cornea and laser delivery system must be applanatic in nature. By definition, an applanatic lens is one that is free from both spherical aberration and coma.

As is recognized by the present invention, applanatic refraction at the anterior surface of the cornea can be effectively accomplished by flattening the anterior surface. With such a corneal reconfiguration, the beam will be free of aberrations (other than chromatic) which would otherwise result from an interface with the cornea's native spherical anterior surface.

Because of the foregoing considerations, a simple mechanical interface device was developed which is the subject of copending parent application Ser. No. 09/772,539. That device is able to stabilize the eye against relative motion with respect to a laser beam used for ophthalmic surgical procedures without relying on secondary mechanical considerations, such as surface tension, friction, or the like. Such a device should be able to present an optical feature to an incident laser beam in a stable, well-characterized location, such that the beam is able to interact with the feature without regard to opto/electronic feedback mechanisms. In addition to maintaining a proper orientation between the eye and a laser delivery system during ophthalmic laser surgery, such a device should applanate the eye during surgery while reducing inter-ocular pressure during the surgical procedure. Such a device should be easy for a clinician to affix, as well as being simple and cost effective to manufacture and use.

Aside from structural differences, applanation lenses are unlike many other types of lenses used in lens systems such as those described in U.S. Pat. Nos. 5,359,373 and 6,142,630, because an applanation lens is not part of an expensive lens system and can easily be removed from mechanical interface devices. As such applanation lenses used in the past have been disposable. Because of cost considerations they have been formed of a polymer materials.

The preferred method of sterilization for such lenses is by gamma sterilization. Gamma sterilization is relatively inexpensive and does not leave a residue, as some sterilizing gases tend to do. However, it has been found that gamma radiation at levels sufficient for sterilization (e.g., 25 kGy–40 kGy) causes problems because it discolors polymers and certain glasses, or otherwise lowers the transmittance of light through these materials. Transmittance as used herein refers to optical efficiency or the ability of a material to transmit light.

Because the dose of radiation may be variable between sterilization lots, the amount of transmittance loss is not uniform. Thus, sterilization of these materials using gamma radiation introduces an uncontrolled variable into the system. This is a serious problem because of the need to be able to focus the laser beam at precise locations in or on the cornea, and to consistently deliver, a predetermined level of energy to that location.

The variability caused by sterilization has the effect of significantly reducing the predictability from one surgical procedure to another, and adds to the time of a surgical procedure because the system must be recalibrated for each use. The loss of transmittance also requires greater power depending on the reduction in the lens's ability to transmit light.

Thus, there is also a need for an applanation lens that remains stable when gamma radiation is applied and does not discolor or lose transmittance below 90% for wavelengths of light from 275 nm to 2500 nm, particularly at about 1053 nm which is the near infrared wavelength of the femtosecond laser that is preferably used in the system in this application.

Because the applanation lens is in direct contact with the cornea of the eye, it must be composed of a material that is biocompatible with corneal tissue. In addition, the applanation lens material must be able to withstand the applied laser energy without melting, oxidizing, or creating byproducts that are not compatible with corneal tissue.

SUMMARY OF THE INVENTION

The problems described above have been solved by an improved applanation lens for use in an interface between a patient's eye and a surgical laser system that does not discolor or lose light transmittance when subjected to gamma radiation. The improved applanation lens has an applanation surface configured to contact the eye and applanate or flatten the anterior surface of the eye upon application of a pressure. The lens is formed of high purity silicon dioxide ($SiO_2$).

The improved applanation lens must have a transmittance of greater than 90% for wavelengths of light from 275 nm–2500 nm, particularly for a wavelength of about 1053 nm. The improved applanation lens is formed of $SiO_2$ with purity great enough to resist discoloration upon prolonged irradiation by high-energy radiation such as UV, x-rays, gamma rays or neutrons, and is preferably a fused silica.

The invention also includes an interface, adapted to couple a patient's eye to a surgical laser, in which the interface includes an attachment apparatus adapted to overlay the anterior surface of an eye and for stable engagement to the eye. An applanation lens, which is adapted to be mounted on the attachment apparatus, has an applanation surface configured to contact the eye and applanate or flatten the anterior surface of the eye upon application of a pressure. The surface is bounded by a plane and coupled to a delivery tip of the surgical laser such that the delivery tip is referenced to the plane. The applanation lens is formed of high purity $SiO_2$ and has an index of refraction of approximately 1.46. The applanation lens must have a transmittance of greater than 90% for wavelengths of light from 275 nm–2500 nm, particularly for a wavelength of about 1053 nm. The applanation lens is formed of a $SiO_2$ with purity great enough to resist discoloration upon prolonged irradiation by high-energy radiation such as UV, x-rays, gamma rays or neutrons, and is preferably a fused silica.

The invention also includes a method for applanating an anterior surface of a patient's eye and coupling the eye to a surgical laser. The method includes the steps of (1) providing an interface, the interface including a central orifice, and having top and bottom surfaces; (2) removably coupling a suction ring to the bottom surface of the interface; (3) positioning the interface over an operative area of an eye, such that the suction ring comes into proximate contact with the surface of the eye; (3) applying a suction to the suction ring to thereby stabilize the position of the interface relative to the operative area of the eye; (4) positioning an applanation lens in proximate contact with the operative area of the eye, the applanation lens having an applanation surface configured to contact the eye and applanate or flatten the anterior surface of the eye upon application of a pressure, the applanation lens being formed of high purity $SiO_2$; and (5) coupling the applanation lens to the interface to thereby stabilize the position of the lens relative to the operative area of the eye. The applanation lens must have a transmittance of greater than 90% for wavelengths of light from 275 nm–2500 nm, particularly for a wavelength of about 1053 nm. The applanation lens is formed of $SiO_2$ with purity great enough to resist discoloration upon prolonged irradiation by high-energy radiation such as UV, x-rays, gamma rays or neutrons, and is preferably a fused silica.

BRIEF DESCRIPTION OF THE DRAWINGS

These and other features, aspects and advantages of the present invention will be more fully understood when considered in connection with the following specification, appended claims and accompanying drawings wherein:

DETAILED DESCRIPTION OF THE INVENTION

The present invention is directed to an improved applanation lens and method using such a lens. The improved lens can be used in any system that uses such a lens, particularly a mechanical apparatus that performs the functions of coupling the anterior surface of a target eye to a surgical laser and applanating said eye. The apparatus is termed mechanical because it directly couples the mechanical surface of an operative target, such as human corneal tissue, to a mechanical fixture of a surgical laser system, such as the distal tip of a laser beam's delivery system. Simply put, and in the context of a particular embodiment which will be described in greater detail below, the apparatus is affixed to the anterior surface of a human cornea and is affixed to the laser delivery system.

Figure 1:
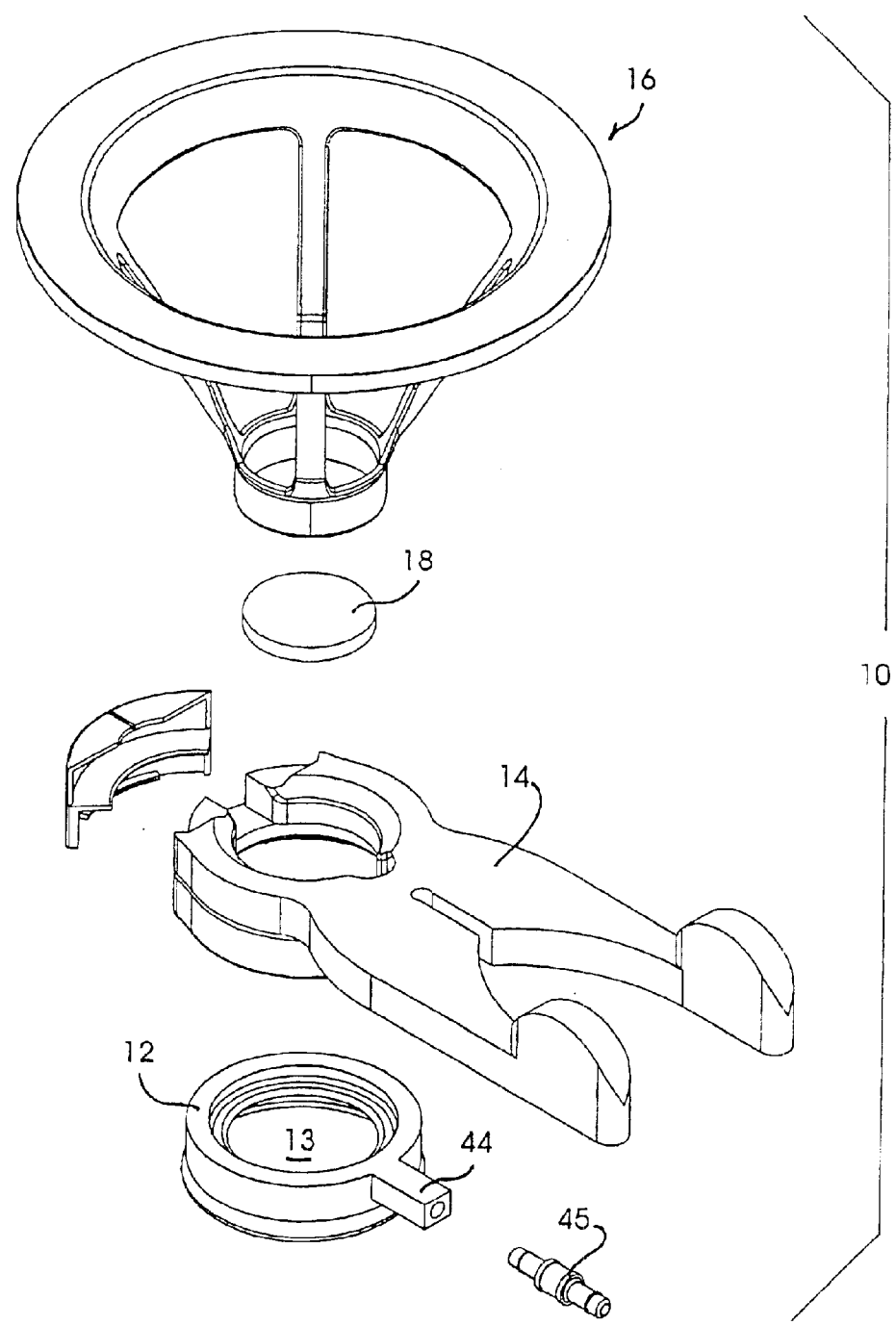
FIG. 1, is an exploded, perspective illustration of the component portions of an ocular stabilization and applanation device in accordance with the present invention.

Referring initially to the exemplary embodiment of FIG. 1, an illustrative ocular fixation and applanation device is shown in an exploded, perspective view, and is generally indicated at 10. The ocular fixation and applanation device (referred to herein as simply an applanation device or alternatively, a patient interface) is an apparatus that attaches to a human eye and holds (fixes) the eye in all three axes (x, y and z) from translational and rotational movement with respect to the incident beam of a laser surgical device. In addition, the applanation device allows for the cornea of the eye to be applanated by a lens (laser optic) for efficient ophthalmic surgery. Once the eye is applanated by an external force, the applanation device grips, holds or affixes the eye to the applanation lens, or laser optic, during a laser surgical procedure, so as to minimize or preclude differential motion of the human eye with respect to the laser optical path during the laser procedure.

With regard to the exemplary embodiment of FIG. 1, the applanation device 10 comprises a number of component parts. In this regard, the applanation device 10 suitably comprises an ocular attachment ring 12, by means of which the applanation device 10 is coupled to the eye, a gripper fixture 14, a lens cone fixture 16 and an applanation lens 18, which in combination with the lens cone 16 is used to applanate a patient's cornea and establish an appropriate optical path alignment between the cornea and a laser optical path.

The component parts of the applanation device 10 are illustrated in exploded view, and are intended to be collapsed vertically, such that each of the individual portions of the device are in mechanical engagement with appropriate other portions, such that the completed device is provided in a generally unitary structure. This is not to say that the device's component parts are permanently affixed to one another: indeed, the component parts are separable and interchangeable at will. Rather, the applanation device 10 is intended to form a single composite interface structure between a human cornea and a surgical laser once the component parts have been aligned with a patient's eye and with respect to the laser delivery system, as will be described in detail below.

As illustrated in the exemplary embodiment of FIG. 1, the attachment ring 12 forms the mechanical interface between the anterior surface of a human cornea and the remaining structure of the applanation device. The attachment ring 12 is constructed of a flexible, hypoallergenic material such as rubber, hypoallergenic plastic, silicone, or the like. The attachment ring 12 is substantially annular in shape, having a generally smooth exterior surface and a highly articulated and functional inner surface, as will be described in greater detail below. Being annular in shape, the attachment ring 12 necessarily defines an outer diameter (OD) and inner diameter (ID), with the inner diameter circumscribing a central target opening 13. The absolute value of its outer diameter is not particularly relevant to practice the principles of the present invention, but the value of the inner diameter is suitably chosen such that when the attachment ring 12 is placed over a patient's eye, the attachment ring's central opening, defined by the inner diameter, completely circumscribes a sufficient area of corneal tissue such that a surgical laser procedure may be completely performed within the exposed area without having to displace the attachment ring.

The attachment ring 12 is disposed and retained within an appropriately shaped female-type receptacle provided in the underside of the gripper/interface structure 14. Since the attachment ring 12 is constructed of a flexible material, the female receptacle of the gripper structure 14 need only have an ID of a dimension slightly smaller than the OD of the attachment ring, such that the attachment ring may fit within the receptacle and be held in place by compressive force.

Figure 2:
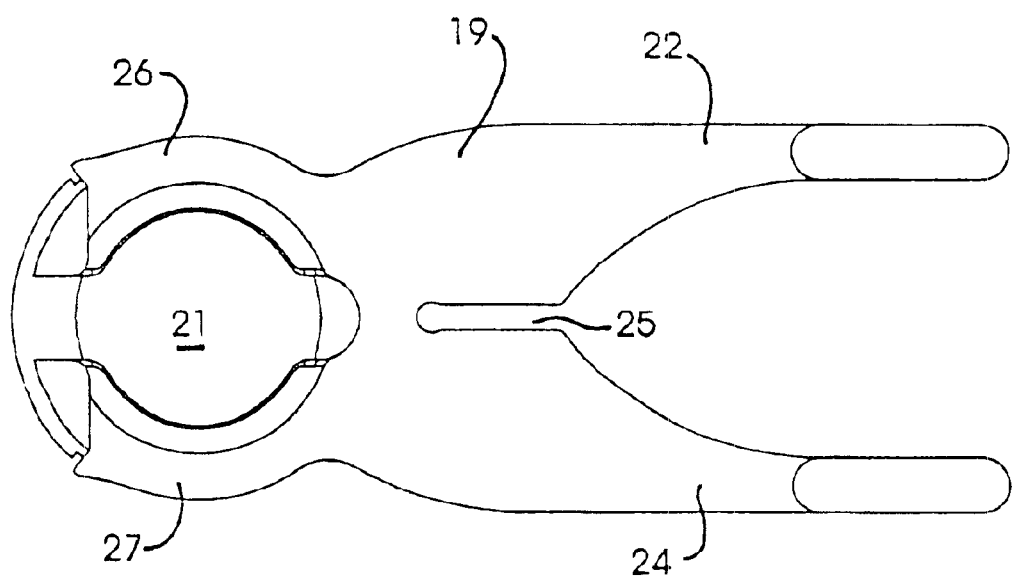
FIG. 2, is a simplified, top plan view of the gripper/interface structure suitable for use in connection with the ocular stabilization and applanation device of FIG. 1.
Figure 3:
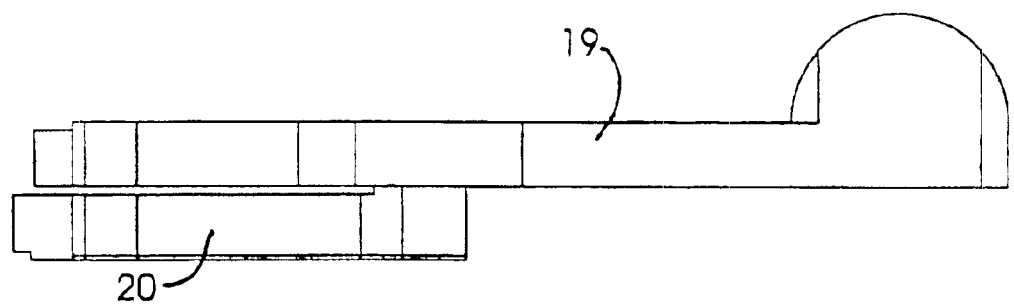
FIG. 3, is a simplified, side view of the gripper/interface structure suitable for use in connection with the ocular stabilization and applanation device of FIG. 1.

The gripper/interface structure 14 of the exemplary embodiment of FIG. 1 is detailed in the top plan view illustration of FIG. 2 and the side view illustration of FIG. 3. In general, the gripper/interface 14 functions much like a clothes pin, and is constructed with a gripper portion 19, overlaying a receiver portion 20 that is designed to receive and contain the attachment ring 12 within a central opening 21 that passes through both the gripper portion and the receiver portion. The gripper portion 19 is constructed as a lever, characterized by two lever handles 22 and 24 separated by a closure spacing 25. As the lever handles are squeezed together, the closure spacing 25 closes and a deformation force is transmitted to two jaws 26 and 27 surrounding the central opening 21. Applying a deformation force causes the jaws 26 and 27 to further separate, in turn causing the central opening to increase in area. Pinching the lever handles 22 and 24 together forces the jaws 26 and 27 to widen sufficiently for a cylindrical object to be inserted into the now-widened central opening 21. Once the pressure on the lever handles is relaxed and the jaws close to their nominal position, the inside surfaces of the jaws 26 and 27 compress against the object and retain the object in position in the central opening 21. The gripper/interface device 14 must couple the attachment ring 12 to the lens cone fixture 16 in a relatively secure manner and with a characterizable geometric relationship.

The receiver portion 20 is disposed below the jaws of the gripper portion and lays in a plane parallel to that of the gripper portion. The receiver portion is cantilevered forward from the space between the lever handles and the jaws and is separated from the gripper jaws by a slight spacing. The receiver portion is substantially annular in shape with the central opening 21 extending therethrough. Thus, it will be noted that when the gripper portion jaws 26 and 27 are opened, only the central opening portion defined in the gripper portion 19 is widened. The central opening portion extending through the receiver portion 20 maintains its diameter. This particular feature allows the attachment ring 12 to be maintained within the central opening portion of the receiving portion, when the gripper jaws are opened. Likewise, the gripper jaws may be opened to receive, for example, the lens cone, without disturbing or displacing the attachment ring.

Figure 4:
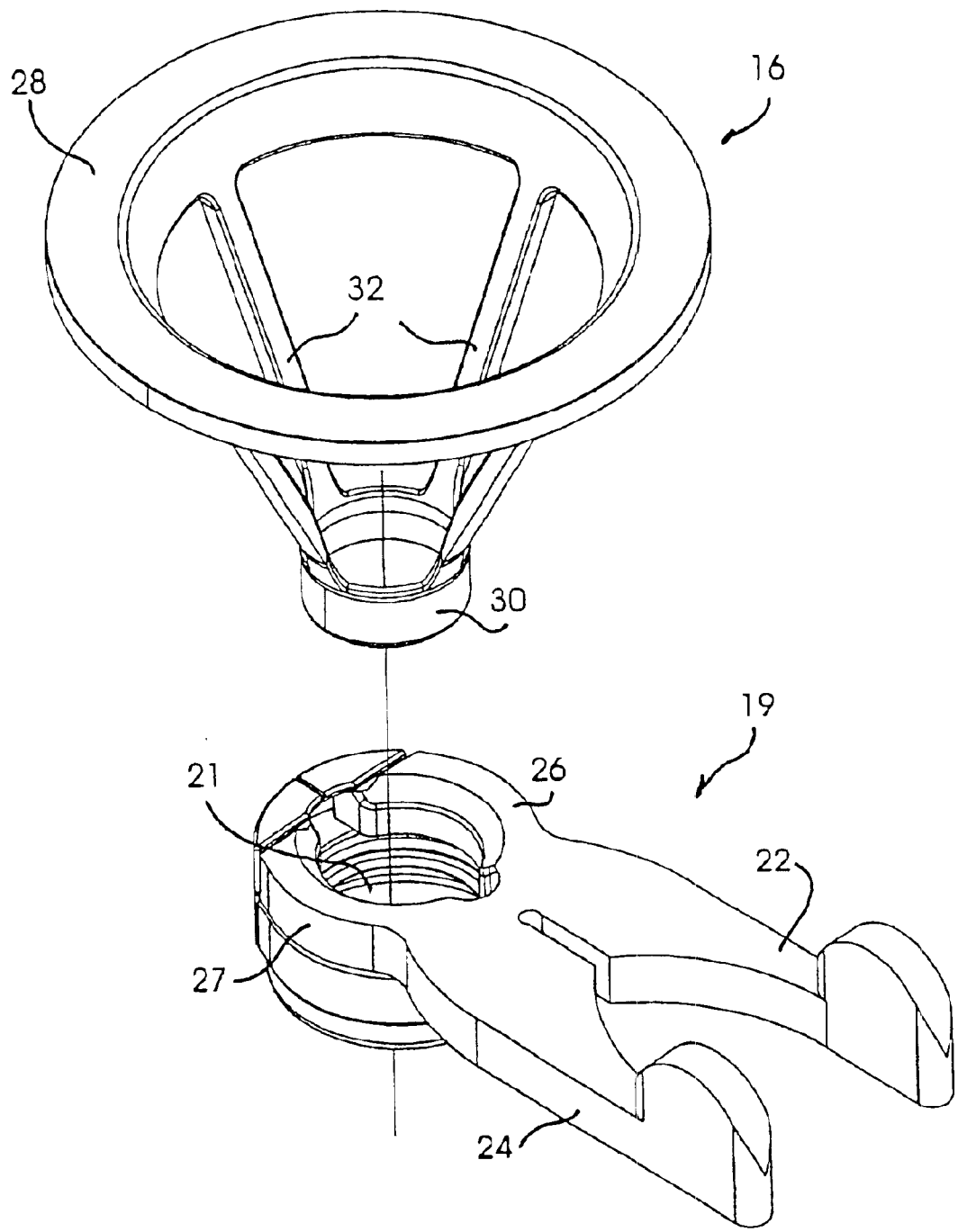
FIG. 4, is a perspective illustration of a lens cone, interfacing with a gripper/interface structure, and incorporating an applanation lens in accordance with the invention.

In this regard, and in connection with the perspective illustration of FIG. 4, the lens cone fixture 16 is suitably constructed as an open-sided truncated cone-like structure, with an open, annular base ring 28 affixed to an open, cylindrical apex ring 30 by a set of support struts 32 which extend between the base ring 28 and the apex ring 30. The base ring 28 is larger than the apex ring 30 thereby giving the lens cone 16 its characteristic truncated cone-like shape.

Being cylindrical in construction, the apex ring 30 will be understood to comprise an inner 20 diameter (ID) and an outer diameter (OD), wherein the OD is dimensioned such that it is only slightly larger than the ID of the central opening portion 21 of the gripper portion 19 of the gripper/interface structure 14. The lens cone structure 16 is constructed of a substantially rigid material such as a rigid, extruded plastic, aluminum, or the like, such that the OD of the apex ring 30 would not be expected to substantially deform under pressure, particularly not under the compression forces applied by the jaws of the gripper.

Accordingly, the lens cone fixture 16 would not precisely fit into the ID of the central opening 21 of the gripper/interface structure 14 under normal circumstances. However, once compressive force is applied to the lever handles 22 and 24, that force is applied to the remainder of the structure, causing the jaws 26 and 27 to open and the interior diameter of central opening 21 to increase in consequence. The OD of the apex ring 30 of the lens cone structure 16 is able to then be inserted into the central opening 21 of the gripper/interface structure I 4 and, when pressure is released on the lever handles 22 and 24, the jaws 26 and 27 close upon the apex ring 30 thereby grasping the apex ring and establishing a fixed relationship between the lens cone 16 and the gripper/interface structure 14. Since the gripper/interface structure 14 is in geometric engagement with the attachment ring 12, and since the attachment ring 12 is coupled to corneal tissue, it should be understood that the lens cone fixture 16 is now held in a particular spatial relationship (alignment) with the surface of the cornea.

As will be described in greater detail below, the apex ring 30 defines a receptacle for receiving and retaining an applanation lens 18. The applanation lens 18 is intended to be placed in proximate contact with a human cornea, and since it is the function of the attachment ring 12 to mechanically interface with a human eye, it should be understood that the gripper/interface structure 14 functions to provide an alignment and coupling interface between the lens cone fixture, including the applanation lens 18, and the attachment ring 12, and thereby the patient's eye.

The applanation lens 18 must have good transmittance (e.g., above 90%) for wavelengths from 275 nm to 2500 nm, preferably at 1053 nm which is the near infrared wavelength of the preferred femtosecond laser used in conjunction with the system described in this application. Because the applanation lens is in direct contact with the cornea of the eye, it must be composed of a material that is biocompatible with corneal tissue. In addition, the applanation lens material must be able to withstand the applied laser energy without melting, oxidizing, or creating byproducts that are not compatible with corneal tissue.

The lens 18 must also be compatible with gamma sterilization and not lose transmittance when exposed to levels of gamma radiation used in the sterilization process (e.g., 25 kGy–40 kGy). Gamma radiation is the preferred method of sterilization to make a lens 18 disposable. Also, the lens 18 must be economically available in quantities and with consistent quality to make production of a disposable lens viable. In view of these considerations, it has been found that an applanation lens 18 formed of high purity $SiO_2$, preferably fused silica, has all of these characteristics. In particular, synthetic fused silica manufactured by Dynasil Corporation, as Dynasil 4000 Fused Silica, is a preferred material.

With regard to the laser delivery system, it will be understood that the base ring portion 28 of the lens cone fixture 16 is adapted to be affixed to the distal end of a laser optical delivery system, such that the delivery system need only be concerned with focusing an incident laser beam at a particular point in space. As will be further described below, the surface of the applanation lens in contact with corneal tissue (the applanation surface) is disposed at a specific distance from the interface between the base ring and the laser delivery system, such that the anterior corneal surface, or at least that portion in contact with the applanation lens, is at a known specific distance from the laser delivery tip. The surface of the cornea now resides along a plane at a distance known to the laser.

Figure 5:
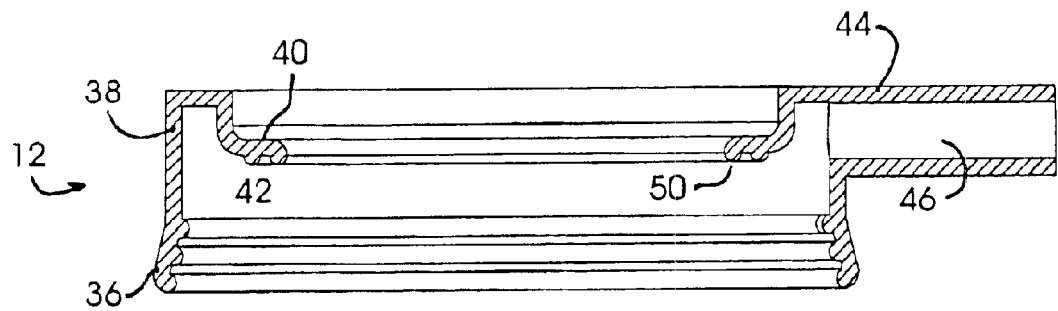
FIG. 5, is a simplified, cross-sectional illustration of an attachment ring, suitable for use in connection with the ocular stabilization and applanation device of FIG. 1.
Figure 6:
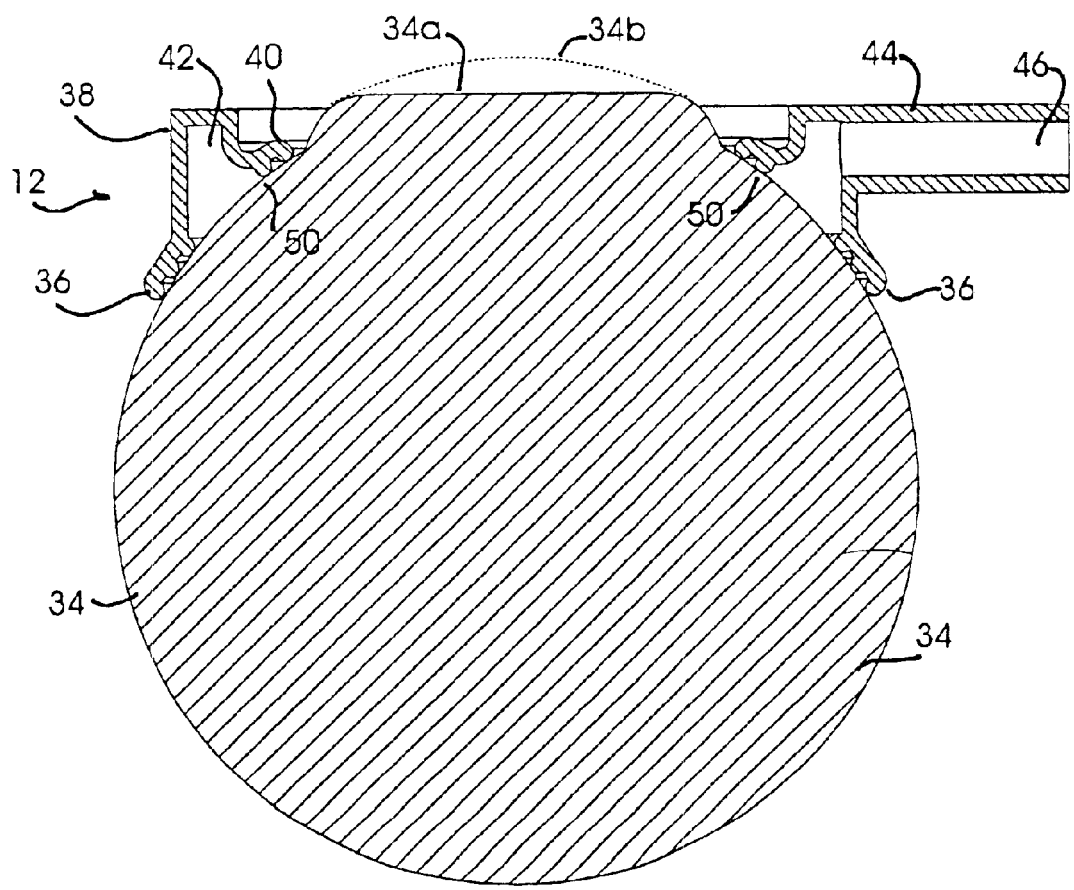
FIG. 6, is a simplified, cross-sectional illustration of the attachment ring of FIG. 5, illustrating the coupling of the attachment ring to the anterior surface of a patient's eye, and indicating applanation of the corneal surface.

An exemplary embodiment of an attachment ring, generally indicated at 12, is illustrated in the exemplary, cross-sectional diagrams of FIGS. 5 and 6, where FIG. 5 illustrates the attachment ring alone, and FIG. 6 illustrates the attachment ring as it would be applied to the anterior surface of a patient's eye. Recall that it is the function of the attachment ring 12 to provide a primary interface with an operative target, such as a human eye, and a laser delivery system. In this regard, the operative target is represented as the corneal portion 34a of a human eye 34 in the exemplary embodiment of FIG. 6, and to which the attachment ring 12 is illustrated as being affixed. In the exemplary embodiment of FIG. 5, the attachment ring 12 is illustrated as having an interior and exterior portion, the exterior portion of which is characterized by a lower skirt 36 which functions as a shroud that comes into intimate contact with the anterior portion of the human eye 34. The shroud 36 has a relatively thin cross-section and is deformable so as to establish and maintain conformal contact with the anterior corneal surface. The shroud or skirt portion 36 extends upwardly into a crown surface 38 which maintains a substantially uniform ID against deformations of the lower shroud portion 36 in response to pressure against the shroud portion by the human eye.

The attachment ring 12 further includes an interior, annular ring member 40 which is disposed on and protrudes outwardly from the interior surface of the attachment ring. The annular ring member 40 protrudes outwardly in a direction normal to the interior surface of the attachment ring, on its top surface, but is formed with a bottom surface that includes an upwardly extending cavity 42, with the cavity formed between a bottom portion of the annular ring member 40 and a proximate portion of the interior surface of the attachment ring 12. Thus, it should be understood that the cavity 42 formed by the shape of the annular ring member 40 defines an annular cavity, with its opening pointing towards the bottom, shroud or skirt portion of the attachment ring.

In the particular exemplary embodiment of FIGS. 5 and 6, the attachment ring 12 further 10 includes an attachment fitting 44 which extends, in a radial direction, from the exterior surface of the attachment ring. The attachment fitting 44 includes a central orifice 46, disposed along its entire length, and which passes through the material of the attachment ring's skirt portion 36, such that a communication path is opened between the annular channel 42, at one end, and the distal end of the attachment fitting 44. The attachment fitting 44 might be constructed of the same material as the attachment ring; indeed the entire apparatus might be formed or molded as single piece. Alternatively, the attachment fitting 44 might be a separate small piece of plastic, metal, or some other material that is coupled to the attachment ring 12 at any stage in the manufacturing or assembly process of the applanation device 10. It should also be noted that if the attachment fitting 44 were to be constructed from the same pliant, flexible rubber, silicone or plastic material as the attachment ring, a suitable female receptacle can be provided on the underside of the gripper structure 14 in proximity to and extending from the central opening 21 thereof. As the attachment ring 12 is friction-fit into place within the gripper 14, the attachment fixture 44 is also press-fit into its corresponding female receptacle, thereby orienting and retaining the entire attachment ring structure within the gripper 14, by compressive force.

Additionally, and as best seen with respect to Fig. I, the attachment fixture 44 might be accessed by inserting one side of a male-to-male fitting coupler 45 (FIG. 1) into the central orifice 46 and coupling the other side to a length of small diameter, medical grade tubing. The tubing is then coupled to a vacuum source which, in turn, is then able to apply a vacuum to the annular channel 42 through the attachment fixture 44. Alternatively, attachment ring 12 may be configured with projections, such as "teeth", "bumps", or some such other gripping or friction inducing structure, that would serve to attach the attachment ring to the eye without the need for suction. In operation, and with regard to the particular exemplary embodiment of FIG. 6, the ocular attachment ring 12 is placed around the limbus of a patient's eye 34, such that its lower, skirt portion 36 surrounds the anterior surface of the cornea 34a, thereby leaving free optical access to the cornea 34a. A slight compressive force is applied to the attachment ring, thereby deforming the skirt portion 36 in an outwardly direction, such that it tends to conform to the shape of the corneal surface. A slight vacuum is developed by a vacuum source or suction pump and coupled to the attachment ring through the attachment fitting 44. As suction is applied to the attachment fitting 44, its internal orifice 46 couples the suction to the annular channel 42 which is now sealed-off from the external ambient environment by corneal contact with the skirt portion 36 (forming one side of the channel) and a contact edge 50 of the annular ring member 40 (forming the other surface of the channel). A vacuum is thereby developed within the annular channel 42 which, in turn, couples the attachment ring 12 to the corneal surface 34a, thereby fixing the eye to the attachment ring which, when it is itself coupled to the rest of the structure, as will be described in greater detail below, fixes the eye against relative movement.

It should be noted, in connection with the embodiment of FIG. 6, that in its preferred form, the attachment ring 12 is affixed to the gripper structure 14, prior to the attachment ring's being coupled to an eye. The gripper is not shown as being already attached to the attachment ring in order that the particular structural and functional details of the attachment ring may be shown simply and without regard to additional and potentially confusing structure. Further, and as will be described in greater detail below, two corneal surface shapes are depicted in the illustrated embodiment of FIG. 6, a rounded surface 34a, indicating the normal shape of the cornea, and a flattened surface 34b indicating the effects of applanating the corneal surface. Applanation is discussed further in this specification, but it is worth noting that as the gripper/ring structure is affixed to the eye 34, the structure surrounds the limbus, leaving the corneal area open to access. The corneal surface remains substantially rounded, at this point, and is only contoured or flattened after introduction of the applanation cone 16 into the gripper and contact is made between the applanation lens 18 and the cornea 34a. The applanated corneal surface 34b then takes on a shape imposed by the shape of the contact surface (applanation surface) of the applanation lens.

In the particular exemplary embodiment of FIG. 6, the vacuum or suction developed by the vacuum source or suction pump is transmitted to the attachment fitting 44 by small-bore tubing. The suction might be applied by coupling the tip of a syringe to the attachment fitting 44 and by introducing a vacuum in the body of the syringe. That vacuum is transmitted to the attachment ring by a small-bore tubing, a blunt canula, or the like. All that is required is that a vacuum (partial or otherwise) be formed within the annular channel 42 such that it is able to provide a coupling force between the attachment ring and the corneal surface.

Figure 7:
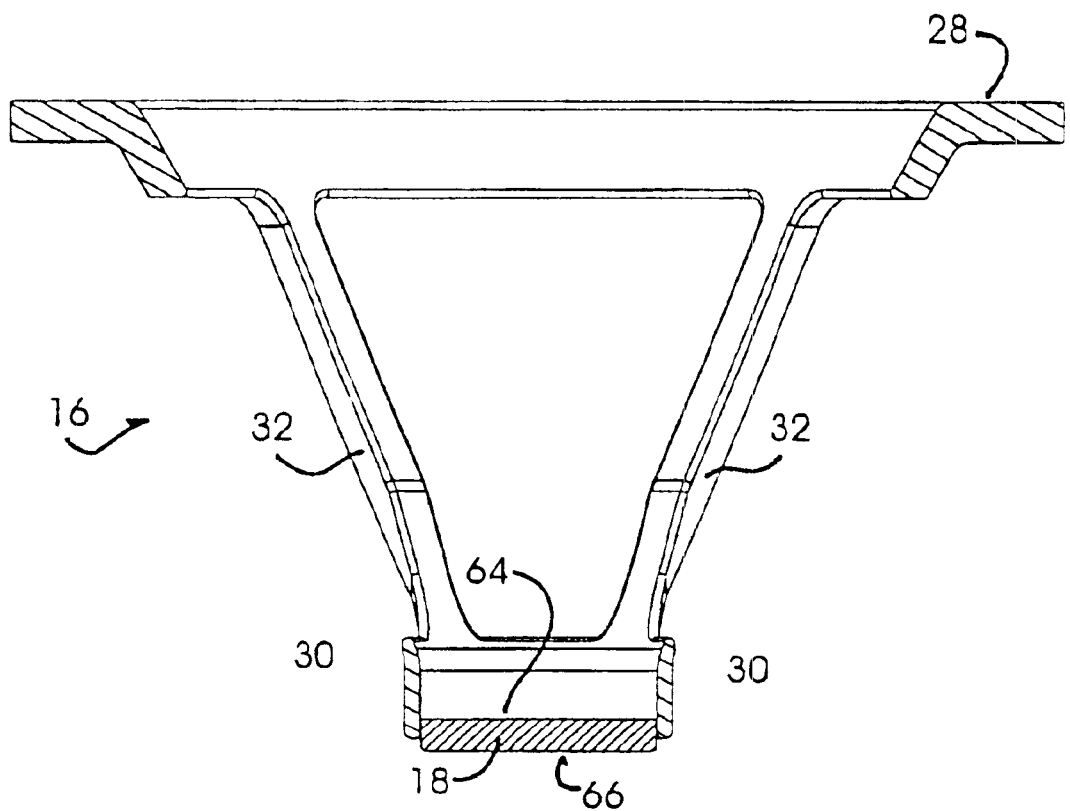
FIG. 7, is a simplified, cross-sectional illustration of a first embodiment of an applanation lens disposed within an attachment ring.

Turning now to FIG. 7, it will be appreciated that the lens cone 16 affords similar functionality to the attachment ring 12, in that the lens cone 16 provides the primary interface and attachment between the applanation device (10 of FIG. 1) and the delivery tip of a surgical laser system. In this regard, the base ring 28 is rigidly coupled to the laser delivery system. Attachment between the two structures may be made in a number of ways, while remaining within the scope of the invention. In particular, the base ring 28 may be provided with slot-shaped cutouts which are mated with retaining pins provided on the delivery system, with the base ring being inserted over the pins and rotated in order to create an interlock. Alternatively, the base ring can be screwed into place on the delivery tip or, the delivery tip might be provided with rotatable "dogs" which are rotated into place over the base ring 28 thereby securing the base ring into position. The means by which the base ring and thus the lens cone 16 are affixed to the delivery tip is not particularly material to practice the principles of the invention. All that is required is that the lens cone 16 be affixed to the delivery tip such that it is incapable of independent relative movement with respect to the delivery tip. In this regard, it should be noted that the base ring has a top surface defining a generally horizontal plane (an x, y plane). The delivery tip is provided with a similar planar surface which is mated with the planar base ring surface. An x, y plane defining one aspect of ocular applanation is thereby established.

As illustrated in the exemplary, cross-sectional diagram of FIG. 7, the lens cone's apex ring 30 extends downwardly away from the base ring 28 and is held in a particular spatial relationship by struts 32, extending between the apex ring 30 and the base ring 28. The base ring 30 is a substantially cylindrical structure with outer and inner wall surfaces and with a wall thickness sufficient to support reasonable rigidity under compressive stress. An applanation lens 18 is disposed within the apex ring 30 and has an OD substantially the same as the ID of the apex ring such that it fits into the apex ring and rests against the ring's interior wall surface. The applanation lens 18 is then bonded into place forming a generally unitary structure with the lens cone 16. The applanation lens 18 is formed with an anterior surface 64 and an applanation surface 66. It is to be appreciated that both the anterior surface 64 and the applanation surface 66 are substantially flat and substantially parallel to one another.

Manufacture of the lens cone involves bonding and alignment of the applanation lens 18 to the apex ring 30. Both of these operations (bonding and alignment) are performed at substantially the same time. The lens cone 16 is placed in registration with an alignment and bonding fixture, termed a "golden pedestal". The golden pedestal has a horizontal alignment plane (an x, y plane) which is positioned parallel to the x, y plane defining the base ring 28. An applanation lens 18 is positioned on the golden pedestal such that its parallel anterior and applanation surfaces lie in the x, y plane defined by the pedestal and, thus the base ring. The lens cone is lowered over the lens until the lens is positioned within the apex ring portion, all the while maintaining the relationship between the various x, y planes. When the lens is in position, it is bonded, with a suitable glue, such as a UV curing cement, to the inside surface of the apex ring, thereby fixing the applanation lens in a specific plane, with respect to the base ring, and at a specific distance from the base ring. Accordingly, it will be appreciated that the applanation lens is established in a specific x, y plane and at a specific z distance from the base ring, itself established in a specific x, y plane and at a specific z distance from the delivery tip of a surgical laser. A known spatial relationship between the laser and the applanation surface of the applanation lens is thereby defined.

The lower, contact, or applanation, surface of the applanation lens is disposed in space in a particular relationship with the laser delivery tip. The contact surface provides a reference surface from which the laser system is able to compute a depth of focus characteristic. Since the position of the contact surface is known, with respect to the delivery tip, so too is the position of the applanated corneal surface. It is, therefore, a relatively straightforward matter to focus a laser beam to any point within the cornea. One needs only to calculate the focal point with respect to the contact surface of the lens, in order that the same focal point be obtained within the eye.

Aligning the lens into position with respect to the lens cone structure by use of a "golden pedestal" allows alignment tolerances which are substantially tighter than those currently obtainable by conventional microkeratome techniques. Conventional microkeratomes typically exhibit off-plane errors in the range of about +/−30 to +/−40 microns. This alignment error leads to planar tilt in the corneal flap, and to potentially dangerous flap thickness variations. For example, if a flap were created with a 30 to 40 micron error, in the positive thickness direction, there exists the possibility that the remaining corneal bed would not be sufficiently thick to safely conduct a laser ablation procedure. Instead the cornea would tend to bulge outward, in response, leading to a less than optimum surface shape being presented for subsequent laser surface ablation. Indeed, it is the very scale of microkeratome depth uncertainty that contributes to the significant percentage of conventional laser surgery failures.

The "golden pedestal" registration and alignment system allows for planar (in both the x, y plane and the z direction) alignment tolerances no greater than that of a conventional microkeratome, i.e., in the range of about +/−30 microns, and preferably in the range of about +/−10 microns. This is measured with respect to both the planar "tilt" and the z position of the applanation surface of the applanation lens with respect to the defined plane of the base ring and, therefore, with respect to the laser's delivery tip. This is particularly advantageous when it is considered that the applanation surface is devised to be co-planar with the anterior surface of the cornea, thereby defining a corneal surface which is mathematically calculable and precise with respect to the laser delivery tip: the x,y plane of the corneal surface is known and the z distance from the tip to the surface is also known. Thus, a precise cut may be made within the corneal material without concern for potentially dangerous depth variation.

Figure 8:
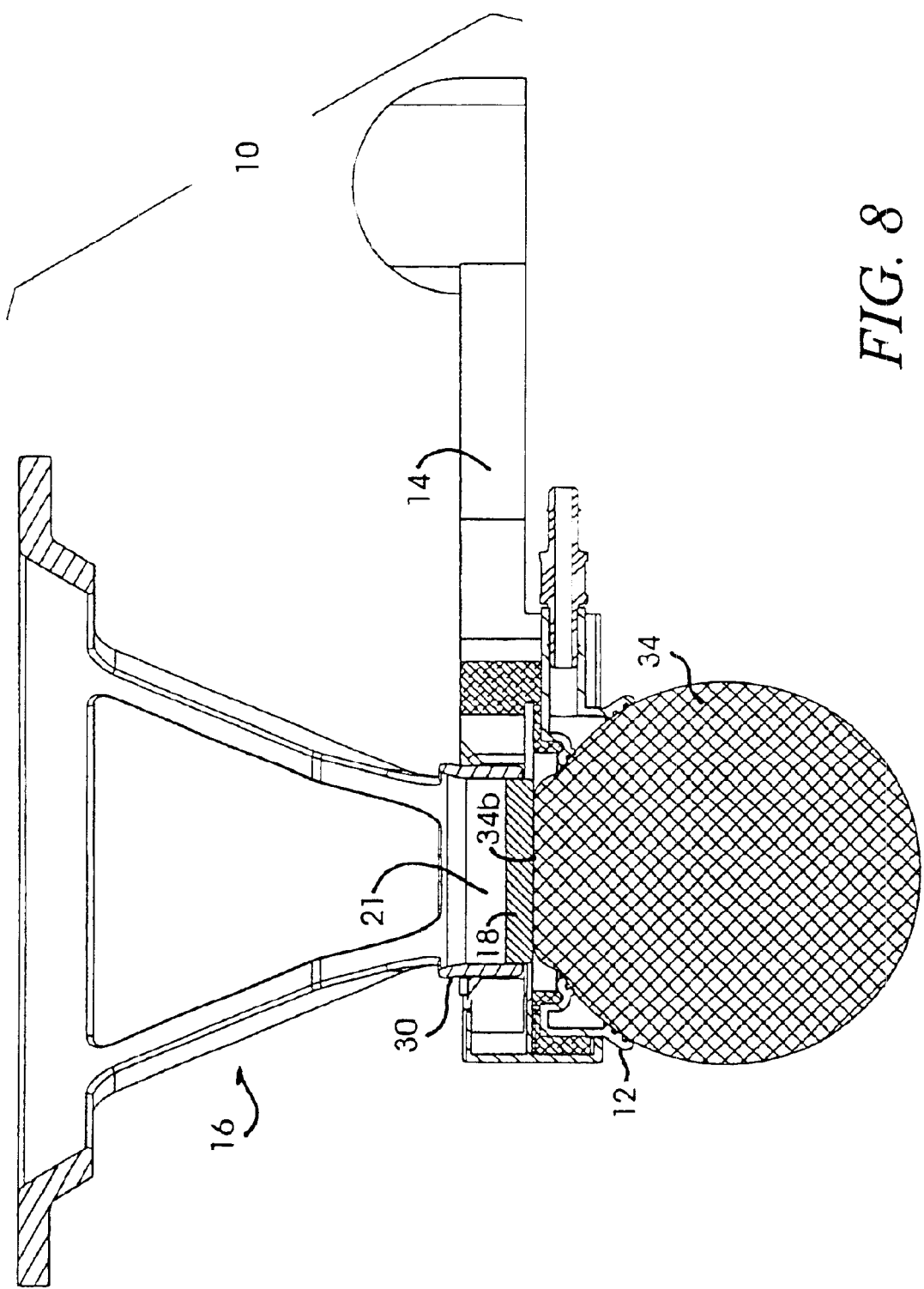
FIG. 8, is a simplified cross-sectional illustration of the ocular stabilization and applanation device of FIG. 1, showing operation of the device to applanate the corneal surface of an eye.

Turning now to FIG. 8, an exemplary embodiment of the complete ocular fixation device 10, as it would be attached to a human eye, is illustrated in cross-sectional form. The lens cone 16 is coupled to the attachment ring 12, thereby coupling a patient's eye 34 to the laser delivery system, by interfacing the two structures together by the gripper/interface 14. As previously mentioned, the apex ring 30 has an OD sized just slightly larger than the ID of the gripper's annular mating portion 20, such that the apex ring 30 can be inserted into the central opening 21 of the gripper 14, when the jaws of the gripper are opened. The apex ring is inserted into the central opening, pressure released on the gripping structures 22 and 24 thereby allowing the jaws to relax and to close around and grip the apex ring 30 securely within the gripper's central opening. As illustrated in the exemplary embodiment of FIG. 8, as the apex ring 30 is inserted into the central opening of the gripper, the applanation surface of the applanation lens makes contact with a presented portion of the anterior surface of the cornea 34b, As the lens cone is lowered into proximity with the cornea, the applanation surface of the lens makes contact with the cornea and applies a pressure to the cornea such that when the lens cone is fully lowered into position, the corneal anterior surface 34b and the applanation surface 66 of the lens are in intimate contact with one another over a substantial portion of the applanation surface. Mechanical pressure of the lens causes the corneal surface to conform to the shape of the applanation surface of the lens. Although depicted in the exemplary embodiment of FIG. 8 as being flat, the cornea may be formed as a concave or convex surface, depending only on the shape of the contact surface of the applanation lens.

In summary, the attachment ring 12 is placed around the limbus of the eye, i.e., centered 10 about the cornea and the pupillary aperture. The gripper 14 has been previously affixed to the attachment ring 12, such that positioning the ring with respect to the eye also positions the eye with respect to the gripper's central opening, with the pupillary aperture generally centered within the gripper's opening. Suction is then applied to the ring in order to attach the ring onto the eye. With the eye so presented and held in place by the attachment ring 12, it becomes a relatively simple matter to lower the lens cone and applanation lens into proximate contact with the cornea, and retain the lens cone, and particularly the applanation lens, in position by fixing the apex ring with the gripper. The gripper is opened to receive the cone assembly which is then lowered into the attachment ring. Simultaneously, the contact surface (applanation surface) of the lens contacts the corneal surface thereby applanating the cornea. The gripper is then closed, thereby clamping the cone assembly in position and fixing the lens relative to the applanated cornea. The eye is held to the gripper by the attachment ring, while the applanation lens is held to the eye by the gripper.

As should be understood from the foregoing, and with respect to the exemplary embodiments, the applanation device is substantially rigidly coupled to the laser delivery system, thus the plane of the applanation surface 66 is characterizable in space with respect to any given focal point of an incident laser beam. With regard to the eye, it should be understood that the applanation lens 18 is able to "float" in the "z" direction due to the flexibility of the skirt portion of the attachment ring. The applanation lens 18 is therefore able to accommodate variously shaped corneal surfaces without placing undue pressure on the eye. Although able to "float" in the "z" dimension, the applanation lens 18 is secured against lateral motion and is accurately disposed in a stable "x,y" plane with respect to the eye.

Figure 9:
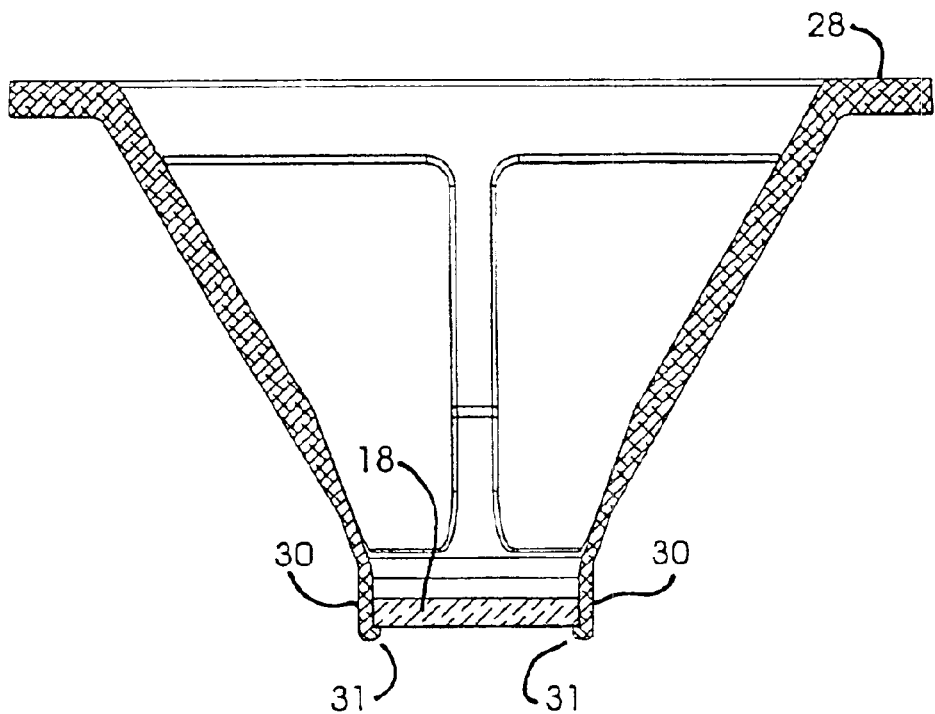
FIG. 9, is a simplified, cross-sectional illustration of a second embodiment of an applanation lens disposed within an attachment ring.

As an alternative embodiment, the applanation lens need not be affixed to the apex ring by a "golden pedestal" approach. As illustrated in the exemplary embodiment of FIG. 9, sufficient alignment of the lens 18 to the plane of the base ring 28 can be accomplished by machining the apex ring 30 to include a retaining lip 31 disposed around the bottom edge of the apex ring. The applanation lens is inserted into the apex ring from the top, and allowed to rest against the retaining lip 31. The lens is now bonded into position using a suitable glue, such as a UV curing cement. Likewise, the retaining lip 31 might be provided as an annular structure circumscribing the interior wall of the apex ring. The lens is inserted from the bottom until its anterior surface rests against the interior lip, at which position it is bonded into place. All that is required in any retaining embodiment, is that the lens be positioned with respect to the lens cone structure such that its alignment in the x, y plane and in the z direction is at least within an approximately +/−30 micron range. In other words, the applanation surface (and therefore the surface of the eye) must be mathematically definable with regard to a laser delivery system to within about +/−30 microns.

An additional alternative embodiment will be appreciated by those having skill in the art, when it is considered that the lens might not be affixed to the lens cone structure prior to the device being assembled on a patient's eye. The applanation lens might be provided as a separate component from the lens cone structure. In this particular embodiment, the applanation lens is constructed as a shallow dish, with sides extending vertically upwards and having an OD such that it may be press-fit within the interior of the annular attachment ring, As the attachment ring and applanation lens combination is fixed to the corneal surface, the applanation lens is able to partially applanate the corneal surface in order to improve alignment. During the initial affixation and alignment procedure, the attachment ring may or may not be fitted within its appropriate receptacle in the gripper structure. The attachment ring, either with or without the applanation lens included, might be first affixed on the patient's eye and the gripper structure lowered over the attachment ring, or, alternatively, the attachment ring, either with or without the applanation lens included, is press fit into its appropriate receptacle on the gripper structure and the entire composite placed over the surface of the patient's eye. In this particular instance, care must be taken to precisely manufacture the bottom surface of the apex ring, since this is the portion of the lens cone which now contacts the applanation lens. Contact pressure between the apex ring and the lens now steadies the lens in the desired plane. Needless to say, the attachment procedures described above hold true for any of the system embodiments described above, as well as one in which the applanation lens is bonded directly to the gripper structure in a suitable position.

After the composite structure is either assembled on the patient's eye, or assembled and then positioned on the patient's eye, the lens cone is lowered into position into the central opening of the gripper and the jaws of the gripper are allowed to relax, thereby grasping and retaining the lens cone in position. As the lens cone is lowered over the structure, final applanation takes place as the applanation lens is either further pressurized against the corneal surface by movement of the lens cone (if the lens is provided as a separate structure) or as the lens is moved into contact with the corneal surface, allowing cone pressure to applanate (if the lens is provided within the lens cone's apex ring), In this regard, it is anticipated that ocular pressure developed by the applanation process will not exceed approximately 60 mmHg, and will preferably be in the range of about 40 to 50 mm Hg.

The lens cone might be secured to the gripper in a number of ways, in addition to being gripped by compressive jaws. For example, the attachment ring might have a communication channel provided between the suction chamber and its interior surface. Accordingly, as the apex ring of the lens cone is lowered into engagement with the attachment ring, a suction is established between the attachment ring and the lens cone's apex ring thereby securing the lens cone to the attachment ring. Although suction involves a relatively simple application of force between the lens cone and attachment ring, suction (or vacuum) is not the only attachment methodology which is contemplated by practice of the invention. Indeed, the upper portion of the attachment ring might be provided with thin, magnetic material that attracts the lens cone's apex ring and provides for secured docking of the lens cone within the attachment ring. Further, the gripper might be provided with a suction manifold disposed around the central opening and the apex ring provided with a flange that overlays manifold openings. As the lens cone is lowered into position, and the flange covers the manifold openings, suction is applied thereby securing the lens cone to the gripper structure. Accordingly, although mating between the lens cone and the gripper/attachment ring has been described in connection with a flexible, press-fitted attachment, a vacuum attachment or a magnetic attachment, it should be understood that the only requirement is that the lens cone is securely held and maintained in a specific spatial relationship with respect to the attachment ring and, consequently, with the corneal surface.

Figure 10:
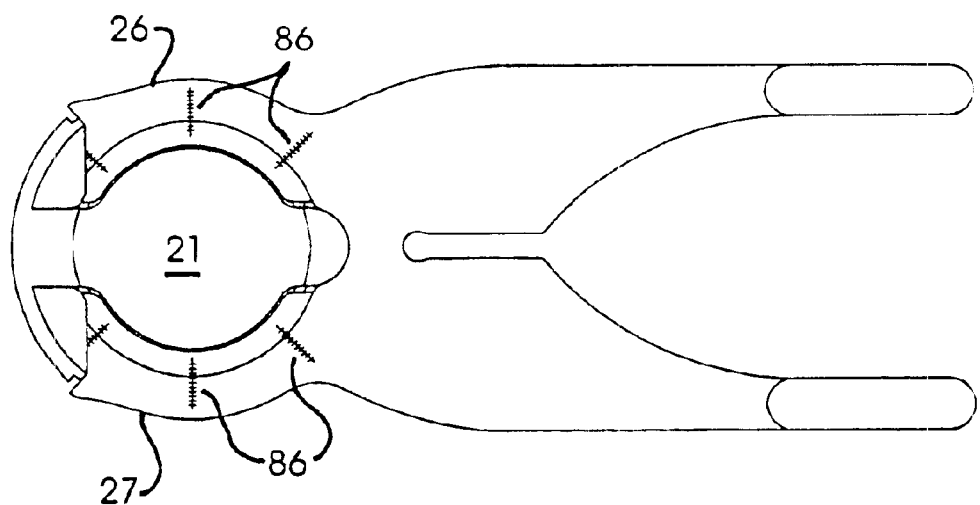
FIG. 10, is a simplified, semi-schematic illustration of the top surface of a gripper/interface device and showing radial alignment guides, in accordance with the present invention.

The present invention has been described, above, primarily with regard to an applanation lens aligned in relation to a human eye in the "z" dimension, while retaining the eye against relative motion along an "x, y" plane. It is also desirable to ensure proper alignment of the structure with regard to the central access of the eye, i.e., allow the structure to centrate about the pupil, such that the iris/pupil is positioned substantially in the center of the central opening of the attachment ring. Turning now to the semi-schematic, top plan view illustration of FIG. 10, the top surface of the gripper 14 (top being the surface opposite that in proximity with the eye) is provided with a set of alignment marks, or fiduciaries, radially disposed about the gripper's central opening 21, on the upper surface of each jaw 26 and 27 and surrounding the central opening 21. The fiduciaries are radially disposed and, if extended towards the center of the opening, aligned such that they will cross at the opening centrum or axis. The alignment marks allow a clinician to judge the central placement of an eye in relation to the opening and eases the clinician's task in accurately positioning the attachment ring/gripper structure with respect to the ocular centrum, before the lens cone is lowered into position for applanation. Once the lens cone is in position, the already aligned gripper laterally aligns the lens, in turn, to the eye. If the structure is appropriately aligned such that the eye is substantially centered within the central opening, a nominal relationship will be established between a laser delivery system and the structural features of an eye in all directions (i.e., x, y, z). This simple mechanical approach obviates the need for complex, highly sophisticated eye following and tracking mechanisms.

A number of exemplary embodiments suitable for practice of the present invention have been described in connection with various illustrations of FIGS. 1–10. However, it should be understood by those having skill in the art that certain modifications, simplifications and expansions may be made without departing from the spirit and scope of the present invention. Specifically, any appropriate laser medium might be used to deliver the incident laser beam without regard to the particular form and shape of the delivery system. In addition, the gripper structure need not be a unitary structure, for example, but may indeed be hinged in a central portion and the gripper jaws opened and closed in response to spring tension and compression made between the gripper handles. Likewise, the applanation lens need not be provided with a substantially flat applanation surface. Depending on the ophthalmic procedure intended to be carried out by the laser system, the lens's applanation surface may be concave or convex in accordance with an appropriate mathematically derived curvature, without departing from the scope and spirit of the invention.

In this particular regard, it will be understood that some degree of spherical aberration might be present in an uncompensated laser beam if the applanation surface of the applanation lens were curved. However, given the mathematical characterizability of the curvature of the applanation surface, it should be understood that a laser beam can be focus-compensated in order to accommodate a degree of curvature.

Accordingly, it is to be understood that the foregoing embodiments are merely illustrative of the invention and that no limitations are intended to either the details of the construction or design other than as defined in the appended claims.

What is claimed is:

1. An improved applanation device specifically adapted for forming a mechanical interface structure between the anterior surface of a patient's cornea and a surgical laser, the improved device comprising:

(a) a frame for holding an applanation lens onto the outer surface of the patient's cornea;

(b) the lens being sized and shaped to be held in the frame and having an applanation surface configured to contact the outer surface of the patient's cornea and provide a reference surface from which the laser is able to compute a depth of focus characteristic, said lens being formed of high purity synthetic fused silicon dioxide ($SiO_2$) such that said lens does not discolor or lose light transmittance when subjected to gamma radiation.

2. The improved applanation lens of claim 1, wherein said applanation lens has a transmittance of greater than 90% for wavelengths of light from 275 nm–2500 nm.

3. The improved applanation lens of claim 2, wherein said applanation lens has a transmittance of greater than 90% for a wavelength of about 1053 nm.

4. The improved applanation lens of claim 1, wherein said applanation lens has an index of refraction of approximately 1.46.

5. The improved applanation lens of claim 1, wherein said applanation lens is formed of an $SiO_2$ with a purity great enough to resist discoloration upon prolonged irradiation by high energy radiation such as gamma rays or neutrons.

6. The improved applanation lens of claim 5, wherein said high purity $SiO_2$ is noncrystalline.

7. A method for applanating an anterior surface of a patient's eye and coupling the eye to a surgical laser, the method comprising the steps of:

a. providing an interface that has been sterilized with gamma radiation, the interface including a central orifice, and an applanation lens having top and bottom surfaces;

b. removably coupling a suction ring to the bottom surface of the interface; positioning the interface over an operative area of an eye, such that the suction ring comes into proximate contact with the surface of the eye;

c. applying a suction to the suction ring to thereby stabilize the position of the interface relative to the operative area of the eye;

d. positioning the applanation lens in proximate contact with the operative area of the eye, said applanation lens having an applanation surface configured to contact the eye said applanation lens being formed of high purity synthetic fused $SiO_2$, such that said applanation lens does not discolor or lose light transmittance when subjected to gamma radiation; and e. coupling the applanation lens to the interface to thereby stabilize the position of the lens relative to the operative area of the eye.

8. The method of claim 7, wherein said applanation lens has a transmittance of greater than 90% for wavelengths of light from 275 nm–2500 nm.

9. The method of claim 8, wherein said applanation lens has a transmittance of greater than 90% for a wavelength of about 1053 nm.

10. The method of claim 7, wherein said applanation lens has an index of refraction of approximately 1.46.

11. The method of claim 7, wherein said applanation lens is formed of an $SiO_2$ with a purity great enough to resist discoloration upon prolonged irradiation by high energy radiation such as gamma rays or neutrons.

12. The method of claim 7, wherein said high purity $SiO_2$ is noncrystalline.

* * * * *